United States Patent [19]

Umeda et al.

[11] Patent Number: 4,603,015

[45] Date of Patent: Jul. 29, 1986

[54] METHOD FOR PRODUCING GLYOXYLYLSPERMIDINE AND THE USE THEREOF FOR THE PRODUCTION OF 15-DEOXY SPERGUALIN-RELATED COMPOUNDS

[75] Inventors: Yoshihisa Umeda, Ootsu; Makoto Moriguchi, Joyo; Teruya Nakamura, Kusatsu; Akio Fujii, Kamakura; Tomio Takeuchi; Hamao Umezawa, both of Tokyo, all of Japan

[73] Assignees: Takara Shuzo Col., Ltd., Kyoto; Nippon Kayaku Kabushiki Kaisha, Tokyo, both of Japan

[21] Appl. No.: 706,168

[22] Filed: Feb. 27, 1985

[30] Foreign Application Priority Data

Feb. 29, 1984 [JP] Japan .................................. 59-36263

[51] Int. Cl.$^4$ ........................ C07C 103/16; C11C 3/00
[52] U.S. Cl. ................................ 260/404.5; 564/201
[58] Field of Search ...................... 564/201; 260/404.5

[56] References Cited

U.S. PATENT DOCUMENTS

| 4,334,073 | 6/1982 | Diehr .............................. 564/201 X |
| 4,334,097 | 6/1982 | Schmidt ............................. 564/201 |
| 4,430,346 | 2/1984 | Umezawa et al. .................. 424/311 |
| 4,448,905 | 5/1984 | Lin et al. .......................... 564/201 X |
| 4,518,802 | 5/1985 | Umezawa et al. .................. 564/201 |

FOREIGN PATENT DOCUMENTS 2111480 7/1983 United Kingdom ........ 564/201 UX

*Primary Examiner*—Paul F. Shaver
*Attorney, Agent, or Firm*—Wenderoth, Lind & Ponack

[57] ABSTRACT

Glyoxylylspermidine, an intermediate for 15-deoxyspergualin-related compounds, is prepared in an oxidative cleavage reaction.

5 Claims, No Drawings

METHOD FOR PRODUCING GLYOXYLYLSPERMIDINE AND THE USE THEREOF FOR THE PRODUCTION OF 15-DEOXY SPERGUALIN-RELATED COMPOUNDS

The present invention relates to a method for producing N-[4-(3-aminopropyl)aminobutyl]-2,2-dihydroxyethaneamide (hereinafter referred to as glyoxylylspermidine) of the following formula (II),

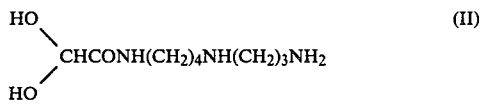

which is a useful intermediate for the synthesis of spergualin-related compounds that are cancerocidal substances and which itself has an immunomodulating effect. The present invention also relates to the use of the above prepared glyoxylylspermidine for the production of cancerocidal (antitumor) substances, i.e. N-[4-(3-aminopropyl)aminobutyl]-2-($\omega$-guanidino fatty acid amide)-2-hydroxyethanamide (hereinafter referred to as "15-deoxy spergualin-related compounds") represented by the general formula (XV):

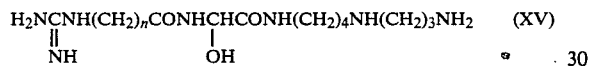

wherein n is an integer from 6 to 8.

Previously, the present inventors proposed a method for producing glyoxylylspermidine by hydrolyzing spergualin, cancerocidal substance, obtained from the culture broth of Bacillus laterosporus BMG 162-aF$_2$ (deposited at Fermentation Research Institute under No. 5230) which is a strain belonging to the genus Bacillus [Japanese Patent Application Kokai (Laid-open) No. 52263/1984; The Journal of Antibiotics, No. 34, 1622 (1981)]. Further, the present inventors proposed an overall synthetic method with 3-amino-1-propanol as one of the starting substances [Japanese Patent Application Kohai (Laid-open) No. 192347/1982; The Journal of Antibiotics, No. 34, 1625 (1981)].

All these methods are excellent method for producing glyoxylylspermidine, but there have been some problems as a method for producing it in large quantities and at low costs in industry.

In the first method with the use of spergualin, a natural substance, as a material, the purification and isolation of spergualin from the culture product of the microorganism were so troublesome that it was difficult to obtain the material in large amounts.

The second method, an overall synthetic method with 3-amino-1-propanol as a starting substance, uses as another material glyoxylic acid of the following formula (III),

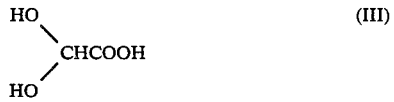

which is difficult to obtain, and besides requires the introduction and removal of an aldehyde-protecting group which are troublesome interms of operation. As the aldehyde-protecting derivative, there may be given for example acetal, thioacetal, hydrozone, oxime and diacyl derivatives.

These conventional synthetic methods passing through a step of protecting the aldehyde group of glyoxylic acid are troublesome in process, so that they had problems as a mass-production method.

An object of the present invention is to provide a simple synthetic method for glyoxylylspermidine. Another object of the invention is to use such glyoxylylspermidine for the production of 15-deoxy spergualin-related compounds.

Briefly speaking, the present invention is directed to a method for producing glyoxylylspermidine of the following formula (II),

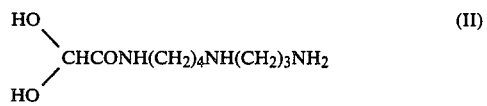

which method is characterized by the selective oxidative cleavage of the appropriate C—C bond of a compound represented by the following general formula (I),

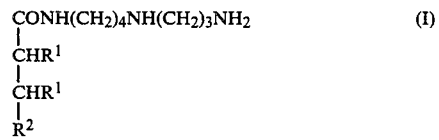

wherein R$^1$ represents a hydroxyl or amino group, but both R$^1$s cannot be amino groups at the same time, and R$^2$ represents a hydrogen atom, an alkyl group which may be substituted, carboxyl group, alkoxycarbonyl group or carbamoyl group which may be substituted.

The present inventors, in order to overcome the problems in the conventional methods, extensively studied a novel method for producing glyoxylylspermidine, and as a result, established a novel method comprising a simple synthetic process and requiring neither protection nor deprotection of the aldehyde group. The present inventors thus completed the present invention.

According to the mechanism of the method of the present invention, the compound represented by the general formula (I), a starting compound, gives the compound of the formula (II) by oxidative cleavage irrespective of a substituent R$^2$. This oxidation reaction itself is a well-known reaction to produce an aldehyde or ketone group by oxidative cleavage of the C—C bond of an adjacent diol or its equivalent functional group. Conventionally employed reagents or methods may be applied to the present invention. As a reagent widely usable for the compound of the general formula (I), periodic acid can be given. When both R$^1$s in the general formula (I) are hydroxyl groups, a reagent properly selected from the group consisting of lead tetraacetate, iodosyl compounds, oxygen in the presence of a catalyst [organic acid cobalt (II) salt], peroxosulfuric acid-silver (I) salt, thallium (III) nitrate, thallium (I) ethoxide, acid cerium (IV) sulfate, bismuthic acid salts, nickel peroxide, etc. may be used along with periodic acid.

So far as the desired reaction proceeds the reaction conditions may be varied depending upon the particular reagents used. Thus, for example, water, acetic acid, trichloroacetic acid, methanol, ethanol, ether, dioxane, benzene, benzonitrile, acetonitrile, pyridine, 4-cyano pyridine, N,N-dimethylformamide, anisole, chlorobenzene, sulfolane, etc. may be used alone or in combination as a solvent for the reaction. The reaction temperature may also vary over a wide range, e.g. from 0° C. up to the boiling point of the solvent used. The reaction time also varies depending upon the particular reaction conditions and generally is from a few minutes to a few days.

Of the above mentioned reagents, periodic acid is particularly preferred as a reagent for oxidative cleavage of the compound represented by the general formula (I) which is a water-soluble compound. For example, it is preferred to use ortho-periodic acid ($H_5IO_6$), sodium meta-periodate ($NaIO_4$) or potassium meta-periodate ($KIO_4$). When these periodic acids are used, the reaction can generally be carried out in aqueous solutions, but it may be carried out in aqueous solutions containing an organic solvent such as alcohols (e.g. methanol, ethanol), dioxane, ether, etc.

The compound represented by the general formula (I), a starting compound for this reaction, can be synthesized by condensing the corresponding acid component having the functional group protected if need arises with the amine component by the well-known reaction to form an amide linkage, and the carrying out deprotection of the functional group if necessary. An acid having a hydroxyl or amino group at the α- and β-positions to be used as a material is available easily and cheaply from a wide range of natural and synthetic compounds. For example, β-hydroxy-α-amino acids (e.g. serine, threonine), polyhydroxymonocarboxylic acids (e.g. glyceric acid, various aldonic acids) and dihydroxydicarboxylic acids (e.g. tartaric acid, α,β-dihydroxyglutaric acid) can be used as a material.

As the amine component, spermidine or a precursor for the synthesis of spermidine having the functional group protected if necessary can be used as a material. For example, 1,5,10-triazadecane having both $N^1$ and $N^5$ atoms protected represented by the following formula (IV),

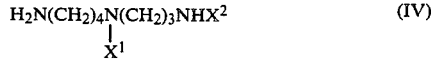

wherein $X^1$ and $X^2$ are each an amino-protecting group, N-(2-cyanoethyl)-1,4-diaminobutane (hereinafter referred to as cyanoethylputrescine) of the following formula (V),

and 1,4-diaminobutane (hereinafter referred to as putrescine) of the following formula (VI),

and the like can be used.

Synthetic examples for the compound represented by the general formula (I) with these acid and amine components will be described hereinafter.

The compound of the general formula (I) wherein $R^1$s are amino and hydroxyl groups and $R^2$ is a hydrogen atom or alkyl group (e.g. methyl group), can be synthesized, for example, by using serine or other suitable amino acid (e.g. threonine) as the acid component and cyanoethylputrescine represented by the formula (V) as the amine component. For example, the compound of the general formula (I) wherein $R^2$ is a hydrogen atom, can be obtained as follows: Serine is first protected at the amino group by the well-known amino-protecting group, for example benzyloxycarbonyl group (Z group) and condensed with cyanoethylputrescine of the formula (V) according to the well-known amide linkage forming reaction to obtain a compound of the following formula (VII),

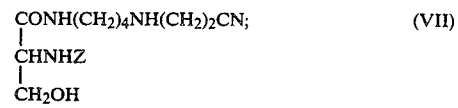

and then after removing the amino-protecting group, the nitrile group is reduced into an aminomethyl group, or after reducing the nitrile group into an aminomethyl group, the amino-protecting group is removed to obtain the desired compound (hereinafter referred to as N-seryl-spermidine).

The compound of the general formula (I) wherein $R^2$ is an alkyl group, for example a methyl group, can be synthesized similarly by using threonine as a material.

The compound of the general formula (I) wherein the both $R^1$s are a hydroxyl group and $R^2$ is a carboxyl group, can be obtained as follows: Diacetyltartaric acid anhydride of the following formula (VIII),

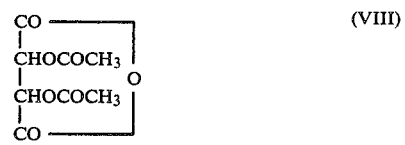

is reacted with putrescine represented by the formula (VI), and the acetyl group is then alkali-hydrolyzed to obtain N-(4-aminobutyl)tartaric acid monoamide of the following formula (IX),

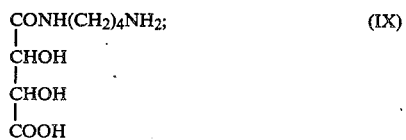

the compound (IX) is N-cyanoethylated by the action of acrylonitrile of the following formula (X),

to obtain N-[4-(2-cyanoethyl)aminobutyl]tartaric acid monoamide of the following formula (XI),

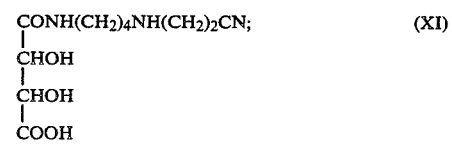

and then the nitrile group of the compound (XI) is reduced into an aminomethyl group to obtain the desired compound.

Further, the compound of the general formula (I) wherein the both $R^1$s are hydroxyl groups and $R^2$ is an alkoxycarbonyl group, can be obtained by esterifying the carboxyl group of the compound (I) obtained by the preceding method as usual, or esterifying the carboxyl group of the compound (XI) as usual and then reducing the nitrile group. Also, the compound of the general formula (I) wherein the both R¹s are a hydroxyl group and R² is a carbamoyl group, can be synthesized by the aminolysis of the compound wherein R² is an alkoxycarbonyl group obtained by the preceding method.

Particularly, the compound of the general formula (I) wherein the both R¹s are hydroxyl groups and R² is a —CONH(CH₂)₄NH(CH₂)₃NH₂ group, can be synthesized in good yield by the following method: Diethyl tartrate of the following formula (XII) easily obtained from tartaric acid by the well-known esterification,

is reacted with cyanoethylputrescine of the formula (V) to obtain N,N'-bis[4-(2-cyanoethyl)aminobutyl]tartaric acid amide of the following formula (XIII),

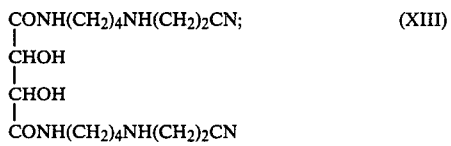

and then the nitrile group of the compound (XIII) is reduced into an aminomethyl group to obtain the desired compound.

As explained above in detail, the method of the present invention, unlike the conventional synthetic methods, requires neither aldehyde-protection nor deprotection for restoring the original aldehyde group of glyoxylylspermidine at the final step, and therefore the process of production can be shortened to a large extent and besides the desired compound can be obtained in good yields. Also, the material for practicing the present invention is cheaply available from a wide range of natural and synthetic compounds.

Thus, the present invention provides a method for producing glyoxylylspermidine at low costs.

By the use of the above produced glyoxylylspermidine there can be produced 15-deoxy spergualin-related compounds more economically and advantageously than before.

Thus, according to the present invention the glyoxylylspermidine of the formula (II) may be condensed with an ω-guanidino fatty acid amide of the general formula (XVI):

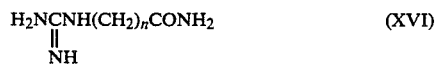

wherein n is an integer of from 6 to 8, to produce 15-deoxy spergualin-related compounds of the formula (XV):

wherein n is as defined above.

The condensation between the glyoxylylspermidine of the formula (II) and the ω-guanidino fatty acid amide of the formula (XVI) may be conducted in a manner described in detail in Japanese Patent Kokai No. 62152/83.

Thus, since this reaction is a dehydration reaction, it is preferable to conduct the same in a solvent free of water. However the compounds of the formulae (II) and (XVI) are usually in the form of acid addition salts and therefore, in view of the solubility, the reaction is conducted in the presence of a small amount of water. The amount of water should be as small as possible so long as the compounds of the formulae (II) and (XVI) are uniformly dissolved and is 4–40 moles per mole of the compound of the formula (II). Since these compounds of the formulae (II) and (XVI) are usually in the form of acid addition salts, it is not necessary to add an acid. However, in view of the yield, it is preferable to use an acid catalyst. Suitable acid catalysts include inorganic acids such as hydrochloric acid, sulfuric aicd, boric acid, etc. and organic acids such as acetic acid, citric acid, tartaric acid, succinic acid, glutaric acid, adipic acid, etc., among which carboxylic acids such as citric acid and glutaric acid are preferable. The amount of an acid to be used is 0 to 10, preferably 0.5–4 moles per mole of the compound of the formula (II). The reaction temperature is from room temperature to 80° C., preferably 40°–60° C. The reaction time varies depending upon the particular reaction temperature and preferably is from a few hours to a few days to obtain a high yield.

The present invention will be illustrated specifically with reference to the following examples, but it is not to be interpreted as being limited to these examples.

EXAMPLE 1

1. Synthesis of N¹-(N'-carbobenzyloxy-L-seryl)-N²-(2-cyanoethyl)-1,4-diaminobutane (VII)

47.8 Grams (0.2 mole) of N-carbobenzyloxy-L-serine was dissolved in 200 ml of dioxane, and after adding 25.3 g (0.22 mole) of N-hydroxysuccinic acid imide thereto, 50 ml of a dioxane solution containing 45.4 g (0.22 mole) of dicyclohexylcarbodiimide (DCC) was added dropwise while cooling with ice under stirring.

After stirring overnight at room temperature, the deposited dicyclohexylurea was removed by filtration, and the filtrate was concentrated under reduced pressure. The resulting residual solid was dissolved in 150 ml of ethyl acetate, and the solution obtained was added dropwise to 300 ml of an ethyl acetate solution containing 42.36 g (0.3 mole) of cyanoethylputrescine (V) with stirring. Thereafter, 300 ml of ethyl acetate was added to the reaction solution, and after stirring overnight, 100 ml of ethyl acetate, 100 ml of a saturated aqueous sodium hydrogencarbonate solution and 50 ml of water were added, followed by stirring for 1 hour.

The reaction solution was separated into an organic and aqueous layers, and the organic layer was washed with 200 ml of a saturated aqueous sodium chloride solution, dried over anhydrous sodium sulfate and concentrated under reduced pressure. The residual solid was dissolved in 50 ml of ethanol, the solution obtained was acidified with conc. hydrochloric acid while cooling with ice, and after standing overnight at 5° C., the deposited product was filtered to obtain 26.7 g of a white crystalline N¹-(N'-carbobenzyloxy-L-seryl)-N²-(2-cyanoethyl)-1,4-diaminobutane (VII).monohydrochloride. The aqueous layer was extracted seven times with 200 ml of ethyl acetate, and the ethyl acetate layer was washed with 200 ml of a saturated aqueous sodium chloride solution, dried over anhydrous sodium sulfate and concentrated under reduced pessure. The residual solid obtained was dissolved in 65 ml of ethanol, and the solution was acidified with conc. hydrochloric acid while cooling with ice, and after standing overnight at 5° C., 34.5 g of the (VII).monohydrochloride was obtained. The sum of the (VII).monohydrochloride was 61.2 g (yield, 76.7%). m.p., 147°–149° C.

NMR(CD$_3$OD):
δ 1.4–1.75(CH$_2$ × 2), 2.4–3.0(CH$_2$N × 2, CH$_2$CN), 3.1–3.4(CONHC$\underline{H}_2$), 3.7(C$\underline{H}_2$OH, d), 4.1–4.3(C$\underline{H}$NH),

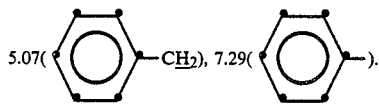

IR(KBr): ν(cm$^{-1}$) 3290, 3060, 2940, 2870, 2240, 1700, 1640, 1540, 1475, 1365, 1300, 1240, 1140, 1100, 1020, 700.

2. Synthesis of N$^1$-L-seryl-N$^2$-(2-cyanoethyl)-1,4-diaminobutane (XIV)

20 Grams (0.05 mole) of N$^2$-(N'-carbobenzyloxy-L-seryl)-N$^2$-(2-cyanoetyl)-1,4-diaminobutane (VII).-monohydrochloride was dissolved in 400 ml of methanol by heating, and after adding 1 g of 10% palladium-carbon, hydrogenolysis was carried out while passing a hydrogen gas at 40° C. for 3 hours. After reaction, a nitrogen gas was passed for 30 minutes, and the catalyst was removed by filtration. After concentrating the filtrate under reduced pressure, the residual solid was dissolved in 100 ml of water, passed through a colum packed with 250 ml of Dowex® 50W×8 (N$^+$ type, produced by Dow Chemical Co.,), and after washing with 1 liter of water, eluted with 2N aqueous ammonia. The active fractions were collected and concentrated under reduced pressure to obtain 9.18 g of a syrup-form N$^1$-L-seryl-N$^2$-(2-cyanoethyl)-1,4-diaminobutane (XIV) (yield, 80.4%).

NMR(CD$_3$OD): δ 1.4–1.8(CH$_2$×2), 2.5–3.05(CH$_2$N×2, CH$_2$CN), 3.2–3.5(CONHCH$_2$, CHNH$_2$), 3.65(CH$_2$OH, d).

IR(KBr): ν(cm$^{-1}$) 3280, 3060, 2930, 2850, 2230, 1650, 1540, 1460, 1360, 1265, 1120, 1050.

3. Synthesis of N-seryl-spermidine (I)

8.82 Grams (38.6 mmoles) of N$^1$-L-seryl-N$^2$-(2-cyanoethyl)-1,4-diaminobutane (XIV) was dissolved in 200 ml of methanol, and after adding 11.04 g (46.4 mmoles), of CoCl$_2$.6H$_2$O thereto, 8.77 g (231.8 mmoles) of NaBH$_4$ was gradually added while cooling with ice. After addition, the reaction solution was stirred at room temperature for 2 hours, and after adding 200 ml of water, adjusted to pH 6.0 with 2N hydrochloric acid. The black deposited product was filtered off, and the filtrate was concentrated under reduced pressure. The residual solid obtained was dissolved in 200 ml of water, passed through a column packed with 2 liters of CM-Sephadex® (produced by Pharmacia Co.), and after washing with 2 liters of water, gradient elution was carried out with 3 liters of water and 3 liters of 1M aqueous NaCl solution. The active fractions were collected and dried to solid under reduced pressure. The residual solid obtained was extracted with methanol, and the methanol extract was passed through a column packed with 500 ml of Sephadex® LH-20 and eluted with methanol. The active fractions were collected and concentrated under reduced pressure to obtain 5.759 g of a syrup-form N-seryl-spermidine (I).trihydrochloride (yield, 43.63%).

NMR(CD$_3$OD): δ 1.5–2.5(CH$_2$×3), 2.9–3.5(CH$_2$N×4), 3.95(CH$_2$OH), 4.1(CHNH$_2$).

IR(KBr): ν(cm$^{-1}$) 3410, 3030, 1670, 1620, 1560, 1460, 1270, 1160, 1060.

4. Synthesis of glyoxylylspermidine (II)

5.55 Grams (16.26 mmoles) of N-seryl-spermidine (I).trihydrochloride was dissolved in 40 ml of water, and 10 ml of an aqueous solution containing 3.55 g (16.58 mmoles) of sodium metaperiodate was added dropwise thereto with stirring at room temperature. After stirring for 45 minutes, the reaction solution was adjusted to pH 1 with 2N hydrochloric acid, stirred for 20 minutes, readjusted to pH 4 with 2N NaOH and passed through a column packed with 500 ml of CM-Sephadex®. Gradient elution was then carried out with 2.5 liters of water and 2.5 liters of 1M aqueous NaCl solution, and the active fractions were collected and dried to solid under reduced pressure. The residual solid obtained was extracted with methanol, and the methanol extract was passed through a column packed with 500 ml of Sephadex® LH-20 and eluted with methanol. The active fractions were collected and concentrated under reduced pressure to obtain 1.583 g of a syrup-form glyoxylylspermidine (II).dihydrochloride (yield, 33.3%).

EXAMPLE 2

1. Synthesis of N-(4-aminobutyl)tartaric acid monoamide (IX)

13.225 Grams (150 mmoles) of putrescine (VI) was dissolved in 75 ml of tetrahydrofuran (THF), and a solution of 10.8 g (50 mmoles) of diacetyl-L-tartaric acid anhydride (VIII) in 50 ml of THF was gradually added dropwise thereto while cooling with ice under stirring. After addition, stirring was continued for 2 hours at room temperature, and after completion of the reaction, the solvent was removed by evaporation under reduced pressure. Thereafter, 50 ml of water was added, and the reaction solution was adjusted to pH 13 with 2N NaOH and stirred at room temperature for 2 hours to effect the hydrolysis of the acetyl group.

The reaction solution obtained was passed through a column packed with 450 ml of Dowex® 1×4[OH$^-$], and after washing with 1.8 liters of water, eluted with 0.5N aqueous acetic acid solution. The fractions containing the objective compound were collected and dried to solid under reduced pressure to obtain 4.03 g of a white crystalline N-(4-aminobutyl)tartaric acid monoamide (IX) (yield, 36.6%).

NMR(D$_2$O): δ 1.4–1.9(CH$_2$×2), 2.98(CH$_2$NHCO, t, J=8 Hz), 3.26(CH$_2$NH, t, J=7.5 Hz), 4.35(CHOH, d, J=2 Hz), 4.49(CHOH, d, J=2 Hz).

IR(KBr): ν(cm$^{-1}$) 3320, 2910, 2850, 1655, 1630, 1550, 1430, 1370, 1310, 1280, 1225, 1130, 1070, 980.

2. Synthesis of N-[4-(2-cyanoethyl)aminobutyl]tartaric acid monoamide (XI)

2.01 Grams (9.127 mmoles) of N-(4-aminobutyl)tartaric acid monoamide (IX) obtained in 1. was dissolved in 40 ml of water, and after adding 1.273 ml of triethylamine and then 0.726 ml of acrylonitrile, the resulting mixture was stirred for 27 hours at room temperature. The reaction solution was then dried to solid under reduced pressure. After adding 20 ml of water to the residual solid, the resulting solution was passed through a column packed with 300 ml of Dowex ® 1×4(OH$^-$), and after washing with 1.2 liters of water, eluted with 0.5N aqueous acetic acid solution. The fractions containing the objective compound were collected and concentrated under reduced pressure to obtain 2.235 g of a syrup-form N-[4-(2-cyanoethyl)aminobutyl]tartaric acid monoamide (XI) (yield, 89.6%).

NMR(DMSO-d$_s$): δ 1.3–1.8(CH$_2$×2), 2.4–3.3(NCH$_2$×3, CH$_2$CN), 4.20(CHOH×2), 7.7(CONH).

IR(KBr): ν(cm$^{-1}$) 3390, 2930, 2230, 1650, 1630, 1540, 1400, 1120, 1070, 600.

3. Synthesis of N-[4-(3-aminopropyl)aminobutyl]tartaric acid monoamide (I)

2.101 Grams (7.688 mmoles) of N-[4-(2-cyanoethyl)aminobutyl]tartaric acid monoamide (XI) obtained in 2. was dissolved in 50 ml of methanol, and after adding 2.195 g (9.226 mmoles) of CoCl$_2$.6H$_2$O, 1.746 g (46.13 mmoles) of NaBH$_4$ was gradually added while cooling with ice under stirring. After addition, stirring was continued for 3 hours at room temperature. After completion of the reaction, 100 ml of water was added, and the reaction solution was adjusted to pH 5.8 with 2N HCl. The deposited black crystal was filtered off, and the filtrate was concentrated under reduced pressure to remove methanol. The concentrated solution was diluted with 50 ml of water and passed through a column packed with 500 ml of CM-Sephadex ® C-25 (Na$^+$), and after washing with 1.5 liters of water, gradient elution was carried out with 2 liters of water and 2 liters of 1M aqueous NaCl solution.

The fractions containing the objective compound were collected, passed through a column packed with 500 ml of Dowex ® 1×4(OH$^-$) and after washing with 2 liters of water, eluted with 0.5N aqueous acetic acid solution. The fractions containing the objective compound were collected and concentrated under reduced pressure to obtain 1.225 g of a red and syrup-form N-[4-(3-aminopropyl)aminobutyl]tartaric acid monoamide (I).acetate (yield, 39.8%).

NMR(D$_2$O): δ 1.4–2.3(CH$_2$×3), 2.8–3.4(NCH$_2$×4), 4.25(CHOH, d, J=2 Hz), 4.4(CHOH, d, J=2 Hz).

IR(KBr): ν(cm$^{-1}$) 3400, 3040, 2950, 1640, 1400, 1120, 1070.

4. Synthesis of glyoxylylspermidine (II)

1.007 Gram (2.985 mmoles) of N-[4-(3-aminopropyl)aminobutyl]tartaric acid monoamide (I).acetate obtained in 3. was dissolved in 80 ml of water, and a solution of 650 mg (3.04 mmoles) of sodium metaperiodate in 20 ml of water was added dropwise with stirring at room temperature. After dropwise addition, stirring was continued for 30 minutes, and the reaction solution was passed through a column packed with 300 ml of CM-Sephadex ® C-25 (Na$^+$) and after washing with 1 liter of water, gradient elution was carried out with 1.5 liters of water and 1.5 liters of 1M aqueous NaCl solution.

The fractions containing the objective compound were collected, dried to solid under reduced pressure, extracted with methanol, and the methanol extract was passed through a column packed with 300 ml of Sephadex ® LH-20 and eluted with methanol. The fractions containing the objective compound were collected and concentrated under reduced pressure to obtain 681 mg of a syrup-form glyoxylyl spermidine (II).-dihydrochloride (yield, 78.1%).

EXAMPLE 3

1. Synthesis of N,N'-bis[4-(2-cyanoethyl)aminobutyl]tartaric acid amide (XIII)

15.45 Grams (0.075 mole) of diethyl L-tartarate (XII) was added dropwise to 23.31 g (0.165 mole) of cyanoethylputrescine (V), and after dropwise addition, the resulting mixture was heated at 80° C. for 2 hours. After cooling the reaction solution with ice, the solidified product was washed with acetone to obtain 29.64 g of N,N'-bis[4-(2-cyanoethyl)aminobutyl]tartaric acid amide (XIII) as a pale yellow crude crystal (yield, 99.8%).

Five grams of this crystal was dissolved in 20 ml of 0.5M aqueous NaCl solution, and the resulting solution was passed through a column containing 1.5 liters of DIAION ® HP-20 (produced by Mitsubishi Chemical Industries, Ltd.) equilibrated with 0.5M aqueous NaCl solution, and successively eluted with 10 liters of water, 5 liters of 5% aqueous methanol and 5 liters of 20% aqueous methanol. The fractions containing the objective compound were collected and concentrated under reduced pressure to obtain 3.1 g of a white crystalline N,N'-bis[4-(2-cyanoethyl)aminobutyl]tartaric acid amide (XIII) (yield, 61.9%).

NMR(DMSO-d$_s$): δ 1.3–1.7(CH$_2$33 4), 2.4–2.9(CH$_2$N×6, CH$_2$CN×2), 3.3–3.7(NH×2, OH×2), 4.20(CH×2), 7.60(CONH×2).

IR(KBr): ν(cm$^{-1}$), 3370, 2905, 2220(CN), 1640, 1520, 1455, 1125.

2. Synthesis of N,N'-bis[4-(3-aminopropyl)aminobutyl]tartaric acid amide (I)

19.8 Grams (50 mmoles) of N,N'-bis[4-(2-cyanoethyl)aminobutyl]tartaric acid amide (XIII) crude crystal obtained in 1. was dissolved in a mixed solution of 450 ml of methanol and 33 ml of water, and after adding 28.55 g (120 mmoles) of CoCl$_2$.6H$_2$O, 22.71 g (600 mmoles) of NaBH$_4$ was added little by little while cooling with ice. After addition of NaBH$_4$, the reaction solution was stirred for 1.5 hours at room temperature, and after adding 200 ml of water, adjusted to pH 6.5 with 6N hydrochloric acid. The deposited black residual solid was filtered off, the filtrate was concentrated under reduced pressure to remove methanol. The concentrated residual solution was diluted to a total volume of 400 ml. Thereafter, 40 ml of the solution thus obtained was passed through a column packed with 500 ml of CM-Sephadex ® C-25 (Na$^+$), and gradient elution was carried out with 3 liters of water and 3 liters of 1.5M aqueous NaCl solution. The fractions containing the objective compound were collected, dried to solid under reduced pressure, extracted with methanol, and the methanol extract was passed through a column packed with 500 ml of Sephadex ® LH-20 and eluted with methanol. The fractions containing the objective compound were collected and dried to solid under reduced pressure to obtain 1.65 g of a syrup-form N,N'- bis[4-(3-aminopropyl)aminobutyl]tartaric acid amide (I).tetrahydrochloride (yield, 60.0%).

NMR(CD$_3$OD): δ 1.5–2.4(CH$_2$×6), 2.9–3.4(NCH$_2$×8), 4.45(CH×2).

IR(KBr): ν(cm$^{-1}$) 3380, 2950, 2800, 1640, 1540, 1460, 1125, 1070, 750.

3. Synthesis of glyoxylylspermidine (II)

An aqueous solution containing 16.04 g (75 mmoles) of sodium metaperiodate was added dropwise to 360 ml of an aqueous solution containing 45 mmoles of the unpurified N,N'-bis[4-(3-aminopropyl)-aminobutyl]tartaric acid amide (I).tetrahydrochloride obtained in 2., and the resulting mixture was stirred for 2 hours at room temperature. After completion of the reaction, 4.5 g (30 mmoles) of L-tartaric acid was added, stirring was carried out for 15 minutes, and the deposited yellowish green product was filtered off. The filtrate was adjusted to pH 5.0 with 2N NaOH, passed through a column packed with 1000 ml of CM-Sephadex ® C-25 (Na$^+$) and after washing with 3 liters of water, gradient elution was carried out with 3 liters of water and 3 liters of 0.6M aqueous NaCl solution. The fractions containing the objective compound were collected, dried to solid under reduced pressure and extracted with methanol. The methanol extract was passed through a column packed with 1000 ml of Sephadex ® LH-20 and eluted with methanol. The fractions containing the objective compound were collected and concentrated under reduced pressure to obtain 8.23 g of a syrup-form glyoxylylspermidine (II).dihydrochloride (yield, 31.3%).

NMR(CD$_3$OD):

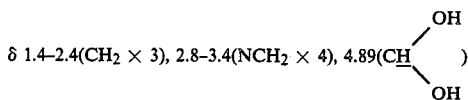

δ 1.4–2.4(CH$_2$ × 3), 2.8–3.4(NCH$_2$ × 4), 4.89(CH)

IR(KBr): ν(cm$^{-1}$) 3370, 2950, 1660, 1540, 1460, 1100, 1070.

EXAMPLE 4

300 Grams (1.45 moles) of diethyl L-tartarate (XII) was added to 450 g (3.19 moles) of cyanoethylputrescine (V), and the resulting mixture was heated at 80° C. for 3 hours. The reaction mixture was dissolved in 4 liters of methanol, and the resulting solution was saturated with ammonia gas while bubbling the gas into the solution while cooling. Subsequently, 180 g of Raney nickel was added, and hydrogenation was carried out at 40° C. for 24 hours under a hydrogen pressure of 12 kg/cm$^2$. After reaction, the catalyst was filtered off, and the filtrate was concentrated under reduced pressure. The syrup obtained was dissolved in 3 liters of water and adjusted to pH 5.0 with 6N hydrochloric acid. To this solution was added in one portion a solution of 397 g (1.66 moles) of sodium metaperiodate in 5 liters of water, and the mixture was stirred at room temperature for 3 hours. After completion of the reaction, 10 ml of ethylene glycol was added to the reaction solution to consume the residual reagent. The solution was then adjusted to pH 5.0 with 6N NaOH, diluted four times with water, passed through a column packed with 12 liters of CM-Sephadex ® C-25 (Na$^+$) and eluted stepwise with 40 liters of 0.1M NaCl and 50 liters of 0.25M NaCl to collect the fraction containing the objective compound. This fraction was diluted four times with water, passed through a column packed with 7.5 liters of CM-Sephadex ® C-25 (Na$^+$) and eluted with 0.8M NaCl. The fractions containing the objective compound were collected and lyophilized. The lyophilized product was extracted with 4 liters of methanol, and the methanol extract was dried to solid under reduced pressure to obtain 400.4 g of a syrup-form glyoxylylspermidine (II).dihydrochloride [overall yield from diethyl tartarate (XII), 43.5%].

EXAMPLE 5

Synthesis of N-[4-(3-aminopropyl)aminobutyl]-2-(7-guanidinoheptanamido)-2-hydroxyethanamide A mixture of 360 mg (1.62 mmoles) of 7-guanidinoheptanamido hydrochloride, 568 mg (1.94 mmoles) of N-[4-(3-aminopropyl)aminobutyl]-2,2-dihydroxyethanamide dihydrochloride obtained in Example 4, 214 mg (1.62 mmoles) of glutaric acid, and 0.36 ml of water was heated at 60° C. for 24 hours. After completion of the reaction, 5 ml of water was added to to the reaction mixture, then passed through a column (20 mm inner diameter) packed with 150 ml of CM-Sephadex ® C-25 (Na-type), and fractionated by the gradient elution with 1.5 liters of water and 1.5 liters of 0.8M aqueous sodium chloride solution. The fractions containing the desired product were combined, then concentrated, and extracted three times with 10 ml of methanol. The methanol layer was passed through a column packed with 150 ml of Sephadex ® LH-20, and developed with methanol. The fractions containing the desired product were combined and evaporated to dryness, yielding 317 mg (39% yield) of white powder of N-[4-(3-aminopropyl)aminobutyl]-2-(7-guanidinoheptanamido)-2-hydroxyethanamide trihydrochloride.

EXAMPLE 6

Synthesis of N-[4-(3-aminopropyl)aminobutyl]-2-(7-guanidinoheptanamido)-2-hydroxyethanamide A mixture of 18 g (80.9 mmoles) of 7-guanidinoheptanamide hydrochloride, 23.6 g (80.9 moles) of N-[4-(3-aminopropyl)aminobutyl]-2,2-dihydroxyethanamide dihydrochloride obtained in Example 4, and 5.7 g (27 mmoles) of citric acid in water (200 ml) was evaporated to dryness to give a syrup which contained 1.6 g of water. The resulting syrup was heated at 60° C. for 8 hours and purifiled in a procedure similar to that in Example 5 giving 19.0 g (47.3% yield) of white powder of N-[4-(3-aminopropyl)aminobutyl]-2-(7-guanidinoheptanamido)-2-hydroxyethanamide trihydrochloride.

EXAMPLE 7

Synthesis of N-[4-(3-aminopropyl)aminobutyl]-2-(9-guanidinononanamido)-2-hydroxyethanamide A mixture of 316 mg (1.26 mmoles) of 9-guanidinononanamide hydrochloride, 442 mg (1.51 mmoles) of N-[4-(3-aminopropyl)aminobutyl]-2,2-dihydroxyethanamide dihydrochloride obtained in Example 4, 166 mg (1.26 mmoles) of glutaric acid, and 0.01 ml of water was heated at 60° C. for 24 hours. After completion of the reaction mixture and the mixture was purified in a manner similar to that in Example 5 using CM-Sephadex ® C-25 (Na-type) and Sephadex ® LH-20, giving 324 mg (49% yield) of white powder of of N-[4-(3-aminopropyl)aminobutyl)]-2-(9-guanidinononanamido)-2-hydroxyethanamide trihydrochloride.

What we claim is:

1. A method for producing N-[4-(3-aminopropyl)-aminobutyl]-2,2-dihydroxyethanamide of the following formula (II),

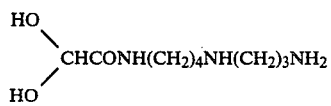

characterized by the selective oxidative cleavage of the appropriate C—C bond of a compound represented by the following general formula (I),

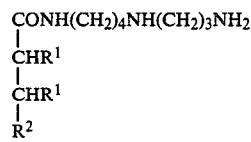

wherein $R^1$ represents a hydroxyl or amino group, but both $R^1$s cannot be amino groups at the same time, and $R^2$ represents a hydrogen atom, an alkyl group which may be substituted, carboxyl group, alkoxycarbonyl group or carbamoyl group which may be substituted.

2. A method for producing the compound of the formula (II) as described in claim 1, wherein the compound represented by the general formula (I) is a compound of the following formula,

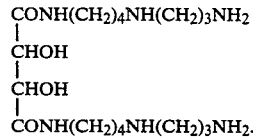

3. A method for producing the compound of the formula (II) as described in claim 1, wherein the compound represented by the general formula (I) is a compound of the following formula,

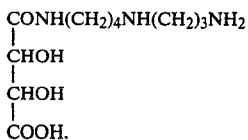

4. A method for producing the compound of the formula (II) as described in claim 1, wherein the compound represented by the general formula (I) is a compound of the following formula,

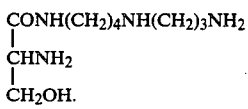

5. A method for producing a compound of the general formula (XV),

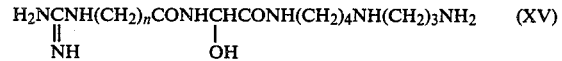

wherein n is an integer of from 6 to 8, which comprises preparing N-[4-(3-aminopropyl)aminobutyl]-2,2-dihydroxy ethanamide of the formula (II),

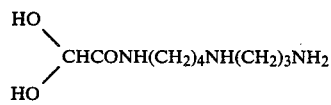

by the oxidative cleavage at the appropriate C—C bond of a compound of the general formula (I),

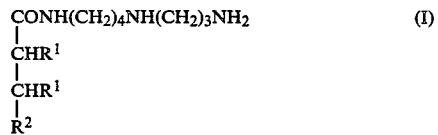

wherein $R^1$ represents a hydroxyl or amino group, but both $R^1$s cannot be amino groups at the same time, $R^2$ represents a hydrogen atom, an alkyl group which may be substituted, carboxyl group, alkoxycarbonyl group or carbamoyl group which may be substituted, and then condensing the above prepared ethanamide of the formula (II) with an ω-guanidino fatty acid amide of the formula (XVI),

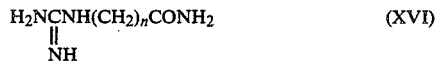

wherein n is as defined above.

* * * * *